United States Patent

Kawaguchi et al.

Patent Number: 5,338,719
Date of Patent: Aug. 16, 1994

[54] PHENOXY OR PYRIDYLOXY-2H-1,4-BENZOXAZINE-3-ONE DERIVATIVE AND HERBICIDE CONTAINING SAME AS ACTIVE INGREDIENT

[75] Inventors: Naoko Kawaguchi, Moriguchi; Harukazu Fukami, Kyoto; Ryuichi Sago, Isehara; Keitaro Ikai, Hiratsuka, all of Japan

[73] Assignee: Suntory Limited, Osaka, Japan

[21] Appl. No.: 48,957

[22] Filed: Apr. 12, 1993

Related U.S. Application Data

[63] Continuation of Ser. No. 738,137, Jul. 30, 1991, abandoned.

[30] Foreign Application Priority Data

Oct. 4, 1990 [JP] Japan .................. 2-265071
Oct. 4, 1990 [JP] Japan .................. 2-265072

[51] Int. Cl.$^5$ ............. C07D 265/36; C07D 413/12; A01N 43/84
[52] U.S. Cl. .................. 504/224; 504/225; 544/105
[58] Field of Search .............. 544/105; 504/224, 225

[56] References Cited

U.S. PATENT DOCUMENTS

| | | | |
|---|---|---|---|
| 3,862,180 | 1/1975 | Jernow et al. | 260/242 |
| 4,618,361 | 10/1986 | Moser | 544/105 |
| 4,721,784 | 1/1988 | Combs | 544/105 |
| 4,885,024 | 12/1989 | Enomoto et al. | 71/92 |
| 4,981,508 | 1/1991 | Strunk et al. | 71/92 |
| 5,141,551 | 8/1992 | Kawaguchi et al. | 504/225 |

FOREIGN PATENT DOCUMENTS

| | | |
|---|---|---|
| 106816 | 4/1984 | European Pat. Off. |
| 243018 | 10/1987 | European Pat. Off. |
| 364141 | 4/1990 | European Pat. Off. |
| 434440 | 6/1991 | European Pat. Off. ........ 544/105 |
| 270707 | 8/1989 | Fed. Rep. of Germany . |
| 2024816 | 9/1970 | France . |
| 2565976 | 12/1985 | France . |

OTHER PUBLICATIONS

Journal of Medicinal Chemistry, 1974, vol. 17, No. 10, pp. 1125–1127, Cox et al.

*Primary Examiner*—Mukund J. Shah
*Assistant Examiner*—Philip I. Datlow
*Attorney, Agent, or Firm*—Burns, Doane, Swecker & Mathis

[57] ABSTRACT

A benzoxazine derivative having the formula (I) and a salt thereof:

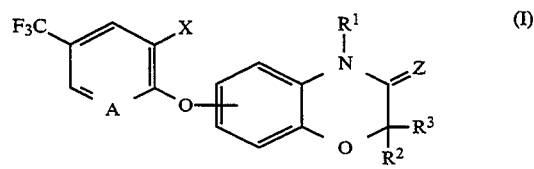

wherein A, X, Z, $R^1$, $R^2$ and $R^3$ are as described in the disclosure, and a herbicide containing the compound of the formula (I) as an effective ingredient.

4 Claims, No Drawings

PHENOXY OR PYRIDYLOXY-2H-1,4-BENZOXAZINE-3-ONE DERIVATIVE AND HERBICIDE CONTAINING SAME AS ACTIVE INGREDIENT

This application is a continuation, of application Ser. No. 07/738,137, filed Jul. 30, 1991, now abandoned.

BACKGROUND OF THE INVENTION

1. Field of the Invention

The present invention relates to a novel benzoxazine derivative, and a herbicide comprising the same as an active ingredient thereof.

2. Description of the Related Art

Although phenoxybenzoxazine derivatives are disclosed in J. Med. Chem., 17 (10), 1125, etc., there is no description therein of a herbicidal effect. Also, the benzoxazine derivatives are greatly different from the above literature compounds, in kind and position of substituents, etc., and are all novel compounds.

SUMMARY OF THE INVENTION

The objects of the present invention are to provide a novel benzoxazine derivative having an excellent herbicidal activity, and a herbicide composition containing the same as an active ingredient thereof.

Other objects and advantages of the present invention will be apparent from the following description.

In accordance with the present invention, there is provided a benzoxazine derivative having the formula (I) and a salt thereof:

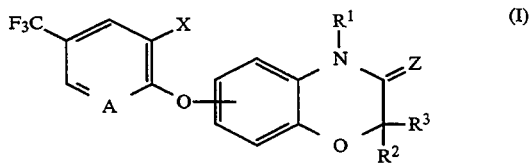

wherein A represents N or a CY group, where Y represents a hydrogen atom or a halogen atom;

X represents a halogen atom;

Z represents an oxygen atom or a sulfur atom;

$R^1$ represents a hydrogen atom, a lower alkyl group which may be also substituted, where the substituent may be either one of a halogen atom, a lower alkoxy group or an aryl group, a lower alkenyl group, a lower alkynyl group or an aliphatic acyl group;

$R^2$ represents a hydrogen atom or a lower alkyl group;

$R^3$ represents a carboxyl group which may be esterified or amidated, an aliphatic acyl group which may be also substituted, where the substituent may be either one of a halogen atom, a diazo group or a hydroxyl group which may be also acylated, a lower alkoxythiocarbonyl group, a $C(=NR^4)R^5$ group, where $R^4$ represents a hydroxyl group, a lower alkoxy group, a lower alkenyloxy group, a lower alkynyloxy group, an amino group, a lower alkylamino group or an alkoxycarbonylalkyloxy group, $R^5$ represents a lower alkyl group, a $C(OR^6)_2R^7$ group where $R^6$ represents a lower alkyl group or a group for forming an alkylen group with two $R^6$'s, $R^7$ represents a lower alkyl group or a $C(R^8)_2OH$ group, where $R^8$ represents a lower alkyl group, and a herbicide composition comprising the same as an active ingredient thereof.

In accordance with the preferred embodiment of the present invention, there is provided a benzoxazine derivative having the formula (IIa) and salt thereof:

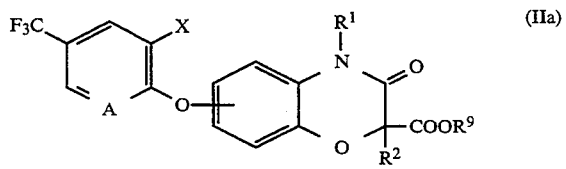

wherein A represents N or a CY group, where Y represents a hydrogen atom or a halogen atom;

X represents a halogen atom;

$R^1$ represents a hydrogen atom, a lower alkyl group which may be also substituted, where the substituent may be either a halogen atom, a lower alkoxy group or an aryl group, a lower alkenyl group, a lower alkynyl group or an aliphatic acyl group;

$R^2$ represents a hydrogen atom or a lower alkyl group;

$R^9$ represents a hydrogen atom, a straight or branched lower alkyl group which may be also substituted, where the substituent may be either a halogen atom, a lower alkoxy group, a lower acyl group, a lower alkoxycarbonyl group or an aryl group, a lower alkenyl group, a lower alkynyl group or an aryl group which may be also substituted, where the substituent may be either a halogen atom or a lower alkyl group.

In accordance with the preferred embodiment of the present invention, there is also provided a benzoxazine derivative having the formula (IIb) and a salt thereof:

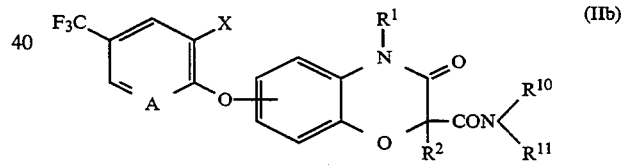

wherein A represents N or a CY group, where Y represents a hydrogen atom or a halogen atom;

X represents a halogen atom;

$R^1$ represents a hydrogen atom, a lower alkyl group which may be also substituted, where the substituent may be either a halogen atom, a lower alkoxy group or an aryl group, a lower alkenyl group, a lower alkynyl group or an aliphatic acyl group;

$R^2$ represents a hydrogen atom or a lower alkyl group;

$R^{10}$ and $R^{11}$, which may be the same or different, each represent a hydrogen atom, a straight, branched or cyclic alkyl group having 1 to 10 carbon atoms which may be also substituted where the substituent may be either a halogen atom, a lower alkoxy group, a lower acyl group, a lower alkoxycarbonyl group or an aryl group, a lower alkenyl group, a lower alkynyl group, an aryl group which may be also substituted, where the substituent may be either a halogen atom or a lower alkyl group, or a heteroaryl group which may be also substituted, where the substituent may be either a halogen atom or a lower alkyl group.

In accordance with the present invention, there is further provided a benzoxazine derivative having the formula (IIc) and a salt thereof:

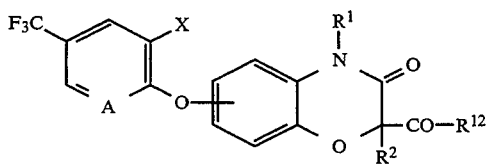

wherein A represents N or a CY group, where Y represents a hydrogen atom or a halogen atom;

X represents a halogen atom;

$R^1$ represents a hydrogen atom, a lower alkyl group which may be also substituted, where the substituent may be either a halogen atom, a lower alkoxy group or an aryl group, a lower alkenyl group, a lower alkynyl group or an aliphatic acyl group;

$R^2$ represents a hydrogen atom or a lower alkyl group;

$R^{12}$ represents a lower alkyl group which may be also substituted, where the substituent may be either a halogen atom, a hydroxyl group, a diazo group or an aliphatic acyloxy group.

In accordance with the preferred embodiment of the present invention, there is further provided a benzoxazine derivative having the formula (IId) and a salt thereof:

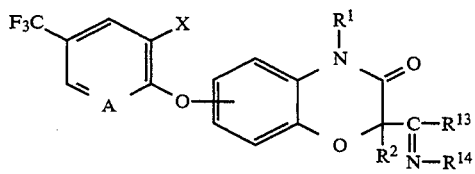

wherein A represents N or a CY group, where Y represents a hydrogen atom or a halogen atom;

X represents a halogen atom;

$R^1$ represents a hydrogen atom, a lower alkyl group which may be also substituted, where the substituent may be either a halogen atom, a lower alkoxy group or an aryl group, a lower alkenyl group, a lower alkynyl group or an aliphatic acyl group;

$R^2$ represents a hydrogen atom or a lower alkyl group;

$R^{13}$ represents a lower alkyl group;

$R^{14}$ represents a hydroxyl group, a lower alkoxy group, a lower alkenyloxy group, a lower alkynyloxy group, a lower alkylamino group or a alkoxycarbonylalkyloxy group.

DESCRIPTION OF THE PREFERRED EMBODIMENTS

The present inventors investigated the herbicidal effect of benzoxazine type compounds, and consequently, found that substituted benzoxazine derivatives having a phenoxy group or pyridyloxy group substituted at the benzene ring have an excellent herbicidal activity, to thus accomplish the present invention.

In the formula (I), the halogen atom represented by X and the halogen atom represented by Y of the group CY represented by A, may be a fluorine atom, chlorine atom, bromine atom or iodine atom.

The lower alkyl group represented by $R^1$ and $R^2$, may be straight or branched alkyl groups having 1 to 5 carbon atoms (e.g., methyl, ethyl, propyl, butyl, pentyl, isopropyl, isobutyl, isopentyl, or sec-butyl).

As the substituent of the lower alkyl group represented by $R^1$, the halogen atom may include one or two or more of a fluorine atom, a chlorine atom, a bromine atom or an iodine atom, the lower alkoxy group may include alkoxy groups having 1 to 5 carbon atoms (e.g., methoxy, ethoxy, propoxy, butoxy, pentyloxy), and the aryl group may include an aryl group having 6–10 carbon atoms (e.g., a phenyl group or a naphthyl group).

The lower alkenyl group represented by $R^1$, may be alkenyl groups having 2 to 5 carbon atoms (e.g., vinyl, 2-propenyl, 3-butenyl, or 4-pentenyl).

The lower alkynyl group represented by $R^1$, may be alkynyl groups having 2 to 5 carbon atoms (e.g., ethynyl, 2-propynyl, 3-butynyl, or 4-pentynyl).

The aliphatic acyl group represented by $R^1$, may be acyl groups having 1 to 5 carbon atoms (e.g., formyl, acetyl, propionyl, butyryl, or valeryl).

In the formula (I), the carboxyl group represented by $R^3$ may be in the form of a free acid or the metal salts thereof, wherein metal salts may include alkali metal salts (for example, sodium, potassium) or alkali-earth metal salts (for example, calcium, magnesium).

The carboxyl group which is esterified and represented by $R^3$ may include straight or branched alkoxycarbonyl groups having 2 to 7 carbon atoms, wherein the straight or branched alkoxy groups may include, for example, methoxy, ethoxy, n-propoxy, n-butoxy, n-pentyloxy, t-butoxy, or isopropoxy, alkenyloxycarbonyl groups having 3 to 6 carbon atoms (wherein alkenyl groups may include, for example, vinyl, allyl, isopropenyl, or isoprenyl, alkynyloxycarbonyl groups having 3 to 6 carbon atoms, wherein the alkynyl groups may include, for example, ethynyl, 2-propynyl, 3-butynyl, or 4-pentynyl, phenoxycarbonyl groups which may be also substituted wherein the substituted phenoxy groups may include, for example, p-chlorophenoxy, m-bromophenoxy, or o-fluorophenoxy, aralkyloxycarbonyl groups having 8 to 10 carbon atoms, wherein aralkyl group may include, for example, benzyl, phenethyl, or phenylpropyl, haloalkyloxycarbonyl groups having 2 to 6 carbon atoms, wherein the haloalkyl groups are methyl, ethyl, propyl, butyl, pentyl substituted with 1 to 3 same or different chlorine atom, bromine atom, iodine atom or fluorine atom including, for example, chloromethyl, difluoromethyl, trifluoromethyl, 2,2,2-trifluoroethyl, or 3,3,3-trifluoropropyl, alkoxyalkyloxycarbonyl groups having 3 to 6 carbon atoms, wherein the alkoxyalkyl group may include, for example, methoxymethyl, methoxyethyl, or ethoxyethyl, alkoxycarbonylalkyloxycarbonyl groups having 3 to 6 carbon atoms, wherein the alkoxycarbonylalkyl group may include, for example, methoxycarbonylmethyl, ethoxycarbonylmethyl, or ethoxycarbonyl-ethyl, amidocarbonylalkyloxycarbonyl groups having 3 to 9 carbon atoms, wherein the amidocarbonylalkyl group may include, for example, amidocarbonylmethyl, ethylamidocarbonylmethyl, dimethylamidocarbonylmethyl, diethylamidocarbonylmethyl, or diethylamidocarbonylethyl or alkylthiocarbonyl groups having 2 to 5 carbon atoms, wherein the alkylthio may include, for example, methylthio, ethylthio or propylthio.

As the carboxyl group, which is also amidated, and represented by $R^3$, there may be included an amidocarbonyl group or primary amidocarbonyl group or secondary amidocarbonyl group bonded with one or two same or different substituents, and the substituents may include straight, branched or cyclic alkyl groups having 1 to 10 carbon atoms (e.g., methyl, ethyl, n-propyl, isopropyl, n-butyl, n-hexyl, n-octyl, or cyclohexyl), alkenyl groups having 2 to 6 carbon atoms (e.g., vinyl, allyl, isopropenyl, or isoprenyl), alkynyl groups having 2 to 6 carbon atoms (e.g., ethynyl, 2-propynyl, 3-butynyl, or 4-pentynyl), aralkyl groups having 7 to 10 carbon atoms (e.g., benzyl, phenethyl, or phenylpropyl), phenyl groups which may be also substituted (e.g., phenyl, p-chlorophenyl, m-bromophenyl, or o-fluorophenyl), heterocyclic groups (e.g., pyridyl, pyrazyl, pyrimidyl, or furyl), haloalkyl groups having 1 to 3 carbon atoms (e.g., a methyl, ethyl or propyl group bonded with 1 to 3 of same or a different chlorine, bromine, iodine or fluorine atom, such as chloromethyl, difluoromethyl, trifluoromethyl, 2,2,2-trifluoroethyl, or 3,3,3-trifluoropropyl), alkoxy groups having 1 to 3 carbon atoms (e.g., methoxy, ethoxy, or propyloxy), alkoxyalkyl groups having 2 to 5 carbon atoms (e.g., methoxymethyl, ethoxymethyl, or ethoxyethyl), esterified or amidated carboxy groups having 2 to 5 carbon atoms (e.g., methoxycarbonyl, ethoxycarbonyl, methylamidocarbonyl, or ethylamidocarbonyl), carboxyalkyl groups which may be also esterified or amidated (e.g., carboxymethyl, methoxycarbonylmethyl, ethoxycarbonylmethyl, ethoxycarbonylethyl, 1-ethoxycarbonylethyl, ethylamidocarbonylmethyl, or 1-ethylamidocarbonylethyl), aliphatic acyl groups having 2 to 5 carbon atoms (e.g., acetyl, propionyl, or butyryl), a methanesulfonyl group, ethylaminothiocarbonyl group, ethoxythiocarbonyl group or dimethylamino group.

The lower alkoxythiocarbonyl group represented by $R^3$ may be, for example, a methoxythiocarbonyl group or ethoxythiocarbonyl group.

The aliphatic acyl group, which may be also substituted, and represented by $R^3$ may be an acyl group having 1 to 5 carbon atoms (e.g., formyl, acetyl, propionyl, butyryl, or valeryl), and examples of the substituents may include a hydroxyl group, acetoxy group, acetoxyacetyloxy group, diazo group or 1 to 3 of the same or different halogen atoms (e.g., chlorine, bromine, fluorine or iodine ).

In the group $C(=NR^4)R^5$ represented by $R^3$, the lower alkoxy group represented by $R^4$ may include alkoxy groups having 1 to 5 carbon atoms (e.g., methoxy, ethoxy, n-propoxy, n-butoxy, n-pentyloxy, t-butoxy, or isopropyloxy); the lower alkenyloxy group represented by $R^4$ may include alkenyloxy groups having 1 to 5 carbon atoms (e.g., vinyloxy, allyloxy isopropenyloxy, or isoprenyloxy), the lower alkynyloxy group represented by $R^4$ may include alkynyloxy groups having 1 to 5 carbon atoms (e.g., ethynyloxy, 2-propynyloxy, 3-butynyloxy, or 4-pentynyloxy); the lower alkylamino group represented by $R^4$ may include alkylamino groups having 1 to 5 carbon atoms (e. g., methylamino, ethylamino, dimethylamino, or diethylamino); and the alkoxycarbonylalkyloxy group represented by $R^4$ may include, for example, a methyl.ethoxycarbonylmethyloxy group. The lower alkyl group represented by $R^5$ may be alkyl groups having 1 to 5 carbon atoms (e.g., methyl, ethyl, n-propyl, isopropyl, or n-butyl, n-hexyl ).

In the group $C(OR^6)_2R^7$ represented by $R^3$, the lower alkyl groups represented by $R^6$ and $R^7$ may include alkyl groups having 1 to 5 carbon atoms ( e.g., methyl, ethyl, n-propyl, isopropyl, n-butyl, or n-hexyl), and the group forming an alkylene group with the two $R^6$'s represented by $R^6$ may include an ethylene group.

In the group, $C(R^8)_2OH$ represented by $R^3$, the lower alkyl group represented by $R^8$ may include alkyl groups having 1 to 5 carbon atoms ( e. g., methyl, ethyl, n-propyl, isopropyl, n-butyl, or n-hexyl ).

The benzoxazine derivative represented by the formula (I) of the present invention can be prepared from the 2-nitrophenol derivative represented by the formula (III), according to the following reaction scheme.

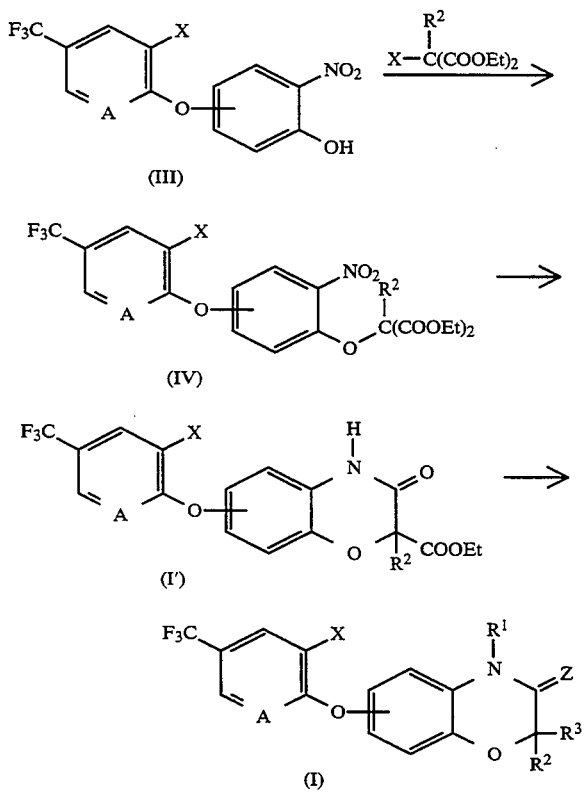

In the reaction scheme, the respective groups represented by A, X, Z, $R^1$, $R^2$ and $R^3$ are the same as defined above.

Thus, the phenoxymalonic acid derivative represented by the formula (IV) can be obtained by reacting an alkali metal salt such as sodium salt of the phenoxy or pyridyloxynitrophenol derivative represented by the formula (III) (U.S. Pat. Nos. 3,798,276 and 3,888,932) with a diethyl halomalonate derivative in an inert solvent such as dimethylformamide (DMF).

The compound (IV) can be catalytically reduced according to a conventional method in an inert solvent such as ethanol, in the presence of a Raney-nickel catalyst, to obtain the benzoxazine derivative (I') which is a part of the present invention.

The compound (I') can be subjected to the reaction as desired by an introduction of a suitable combination of various substituents into the 4-position nitrogen atom (alkylation or acylation), a conversion of the 3-position carbonyl group to a thiocarbonyl group, and a conversion of the 2-position ethoxycarbonyl group to various derivatives (e.g., hydrolysis, esterification, amidation, Grignard reaction, imidation, etc.) to obtain the compound represented by the formula (I) of the present invention.

Various optical isomers based on the substituents exist in the compound (I) of the present invention, and these are all included in the present invention.

EXAMPLES

The present invention will now be further illustrated by, but is by no means limited to, the following Examples and Reference Examples.

Example 1

Ethyl 7-(2-chloro-4-trifluoromethylphenoxy)-3,4-dihyrdo-3-oxo-2H-1,4-benzoxazine-2-carboxylate (Compound 1)

Diethyl 2-[5-(2-chloro-4-trifluoromethylphenoxy)-2-nitrophenoxy]malonate (Reference compound IV-1) (2.0 g) was dissolved in ethanol (20 ml), and a hydrogenation was carried out, with addition of Raney nickel as the catalyst, at room temperature under normal pressure for 10 hours. The reaction mixture was filtered, the filtrate concentrated under a reduced pressure, and the residue obtained was purified by silica gel chromatography (eluant: n-hexane/ethyl acetate=3/1) to give 0.9 g of the title compound (colorless crystals).

In Example 1, by carrying out a similar reaction using Reference example compound IV-2, Reference example compound IV-3, Reference example compound IV-4 and Reference example compound IV-5, in place of Reference compound IV-1, ethyl 7-(2-chloro-4-trifluoromethylphenoxy)-2-methyl-3,4-dihydro-3-oxo-2H-1,4-benzoxazine-2-carboxylate (Compound 2), ethyl 7-(2,6-dichloro-4-trifluoromethylphenoxy)-2-methyl-3,4-dihydro-3-oxo-2H-1,4-benzoxazine-2-carboxylate (Compound 3), ethyl 7-(2-chloro-6-fluoro-4-trifluoromethylphenoxy)-2-methyl-3,4-dihydro-3-oxo-2H-1,4-benzoxazine-2-carboxylate (Compound 4), and ethyl 6-(3-chloro-5-trifluoromethylpyridin-2-yloxy)-3,4-dihydro-3-oxo-2H-1,4-benzoxazine-2-carboxylate (Compound 5) were obtained.

Example 2

Ethyl 7-(2-chloro-4-trifluoromethylphenoxy)-4-methyl-3,4-dihydro-3-oxo-2H-1,4-benzoxazine-2-carboxylate (Compound 6)

60% Sodium hydride (1.0 g) was suspended in dimethylformamide (hereinafter abbreviated as DMF) (5 ml) and under ice-cooling, a DMF solution (5 ml) of ethyl 7-(2-chloro-4-trifluoromethylphenoxy)-3,4-dihydro-3-oxo-2H-1,4-benzoxazine-2-carboxylate (Compound 1) (0.8 g) was dropwise added thereto, followed by stirring for 10 minutes. Methyl iodide (0.4 g) was then added, the mixture was further stirred for 10 minutes, and to the reaction mixture was added water (20 ml) and the mixture was extracted twice with ethyl acetate (50 ml). The extract was washed with water and then saturated aqueous sodium chloride, and dried over magnesium sulfate. The solvent was then evaporated under a reduced pressure and the residue was purified by silica gel chromatography (eluant: n-hexane/ethyl acetate=3/1) to give 0.4 g of the title compound (colorless oil).

In Example 2, by using two-fold amounts of sodium hydride and methyl iodide and carrying out the reaction in the same manner, ethyl 7-(2-chloro-4-trifluoromethylphenoxy)-2,4-dimethyl-3,4-dihydro-3-oxo-2H-1,4-benzoxazine-2-carboxylate (Compound 7) was obtained, and using a two-fold amount of ethyl bromide in place of methyl iodide, ethyl 7-(2-chloro-4-trifluoromethylphenoxy)-2,4-diethyl-3,4-dihydro-3-oxo-2H-1,4-benzoxazne-2-carboxylate (Compound 8) was obtained.

Example 3

Ethyl 7-(2,6-dichlor-2-methyl-4-trifluoromethylphenoxy)-4-difluoromethyl-3,4-dihydro-3-oxo-2H-1,4-benzoxazine-2-carboxylate (Compound 20).

To a DMF solution (50 ml) of ethyl 7-(2,6-dichloro-4-trifluoromethylphenoxy)-2-methyl-3,4-dihydro-3-oxo-2H-1,4-benzoxazine-2-carboxylate (Compound 3) (1.5 g) was added 60% sodium hydride (0.2 g), and the mixture was stirred for one hour. Then, while cooling in a dry ice-acetone bath, chlorodifluoromethane gas was introduced for one hour, and the mixture then stirred for 2 days and nights. Thereafter, water (50 ml) was added and the mixture was extracted twice with ethyl acetate (50 ml), and the extract was washed with water and then with saturated aqueous sodium chloride, and then dried over magnesium sulfate. The solvent was evaporated under a reduced pressure, and the residue was purified by silica gel chromatography (eluant: n-hexane/ethyl acetate=9/1) to give 0.6 g of the title compound (colorless oil).

Example 4

Ethyl 7-(2-chloro-4-trifluoromethylphenoxy)-3,4-dihydro-3-thio-2H-1,4-benzoxazine-2-thiocarboxylate (Compound 21)

Ethyl 7-(2-chloro-4-trifluoromethylphenoxy)-3,4-dihydro-3-oxo-2H-1,4-benzoxazine-2-carboxylate (Compound 1) (0.4 g) was dissolved in toluene (5 ml), and 2,4-bis(4-methoxyphenyl)-1,3-dithia-2,4-diphosphetane-2,4-disulfide (Lawson reagent) (0.2 g) was added to the solution, followed by heating under reflux for 2 hours. The solvent was then evaporated under a reduced pressure, and the residue was purified by silica gel chromatography (eluant: n-hexane/ethyl acetate=5/1) to give 0.4 g of the title compound (colorless crystals).

Example 5

7-(2-Chloro-4-trifluoromethylphenoxy)-2,4-dimethyl-3,4-dihydro-3-oxo-2H-1,4-benzoxazine-2-carboxylic acid (Compound 23)

Ethyl 7-(2-chloro-4-trifluoromethylphenoxy)-2,4-dimethyl-4-methyl-3,4-dihydro-3-oxo-2H-1,4-benzoxazine-2-carboxylate (Compound 7) (1.1 g) was dissolved in methanol (10 ml), 1N sodium hydroxide (3 ml) was added thereto, and the mixture was stirred at room temperature for 2 hours. Then 1N hydrochloric acid (5 ml) was added, the solvent was evaporated under a reduced pressure, and the residue was extracted twice with ethyl acetate (20 ml). The extract was washed with water and then with saturated aqueous sodium chloride, and dried over magnesium sulfate, followed by an evaporation of the solvent under a reduced pressure to give 0.9 g of the title compound (colorless oil).

Example 6

Methyl 7-(2-chloro-4-trifluoromethylphenoxy)-2,4-dimethyl-3,4-dihydro-3-oxo-2H-1,4-benzoxazine-2-carboxylate (Compound 29)

7-(2-Chloro-4-trifluoromethylphenoxy)-2,4-dimethyl-3,4-dihydro-3-oxo-2H-1,4-benzoxazine-2-carboxylic acid (Compound 23) (0.4 g) was dissolved in benzene (10 ml), and thionyl chloride (2 ml) was added thereto, followed by heating under reflux for 3 hours. The solvent was then evaporated under a reduced pressure, methanol (5 ml) was added thereto, and the mixture was stirred at room temperature for one hour. The solvent was then evaporated under a reduced pressure, and the residue was purified by use of silica gel chromatography (eluant: n-hexane/ethyl acetate= 3/1) to give 0.2 g of the title compound (colorless crystals).

Example 7

Methoxycarbonylmethyl 7-(2-chloro-4-trifluoromethylphenoxy)-2,4-dimethyl-3,4-dihydro-3-oxo-2H-1,4-benzoxazine-2-carboxylate (Compound 46)

7-(2-Chloro-4-trifluoromethylphenoxy)-2,4-dimethyl-3,4-dihydro-3-oxo-2H-1,4-benzoxazine-2-carboxylic acid (Compound 23) (0.4 g) was dissolved in DMF (0.2 ml) and dicyclohexylamine (0.2 ml) was added thereto, followed by stirring at 60° C. for 15 minutes. Then methyl bromoacetate (0.2 g) was added, the mixture further stirred at 60° C. for 3 hours, to the reaction mixture was added water (20 ml), and the mixture was extracted twice with ethyl acetate (20 ml). The extract was washed with water and then with saturated aqueous sodium chloride, and then dried over magnesium sulfate, followed by an evaporation of the solvent under a reduced pressure. The residue was purified by silica gel chromatography (eluant: n-hexane/ethyl acetate=3/1) to give 0.3 g of the title compound (colorless crystals).

Example 8

(Ethylamidocarbonyl)methyl 7-(2-chloro-6-fluoro-4-trifluoromethylphenoxy)-2,4-dimethyl-3,4-dihydro-3-oxo-2H-1,4-benzoxazine-2-carboxylate (Compound 47)

To a dichloromethane solution (20 ml) of glycolic acid (0.3 g) and triethylamine (1.0 ml) was added an acid chloride (1.5 g) prepared as in Example 6 from 7-(2-chloro-6-fluoro-4-trifluoromethylphenoxy)-2,4-dimethyl-3,4-dihydro-3-oxo-2H-1,4-benzoxazine-2-carboxylic acid (Compound 25), and the mixture was stirred at room temperature for one hour. The reaction mixture was then concentrated under a reduced pressure, the residue was extracted twice with ethyl acetate (20 ml), and the extract was washed with water and then with saturated aqueous sodium chloride, and dried over magnesium sulfate, followed by evaporation of the solvent under a reduced pressure to obtain carboxymethyl 7-(2-chloro-6-fluoro-4-trifluoromethylphenoxy)-2,4-dimethyl-3,4-dihydro-3-oxo-2H-1,4-benzoxazine-2-carboxylate. The acid was dissolved in benzene (20 ml), thionyl chloride (0.9 g) was added thereto, and the mixture was heated under reflux for 3 hours. Then after an evaporation of the solvent under a reduced pressure, the residue was dissolved in dichloromethane (20 ml), ethylamine hydrochloride (0.6 g) and triethylamine (2 ml) were added thereto, and the mixture was stirred for one hour. The reaction mixture was then concentrated under a reduced pressure, and the residue was extracted twice with ethyl acetate (20 ml). The extract was washed with water and then with saturated aqueous sodium chloride, and dried over magnesium sulfate, followed by an evaporation of the solvent under a reduced pressure. The residue was purified by silica gel chromatography (eluant: n-hexane/ethyl acetate=3/1) to give 0.5 g of the title compound (colorless oil).

Example 9

7-(2-chloro-4-trifluoromethylphenoxy)-2,4-dimethyl-3,4-dihydro-3-oxo-2H-1,4-benzoxazine-2-carboxyamide (Compound 48)

An acid chloride (0.4 g) prepared in the same manner as in Example 6 from 7-(2-chloro-4-trifluoromethylphenoxy)-2,4-dimethyl-3,4-dihydro-3-oxo-2H-1,4-benzoxazine-2-carboxylic acid (Compound 23) was dissolved in tetrahydrofuran (hereinafter abbreviated as THF) (5 ml), and the solution was stirred while blowing ammonia gas therein for one hour. Then, after an evaporation of the solvent, the residue was purified by silica gel chromatography (eluant: n-hexane/ethyl acetate=1/1) to give 0.3 g of the title compound (colorless crystals).

Example 10

N-ethyl-7-(2-chloro-4-trifluoromethylphenoxy)-2,4-dimethyl-3,4-dihydro-3-oxo-2H-1,4-benzoxazine-2-carboxyamide (Compound 49)

An acid chloride (0.4 g) prepared in the same manner as in Example 6 from 7-(2-chloro-4-trifluoromethylphenoxy)-2,4-dimethyl-3,4-dihydro-3-oxo-2H-1,4-benzoxazine-2-carboxylic acid (Compound 23) was dissolved in dioxane (5 ml), and ethylamine hydrochloride (0.1 g) was added thereto, followed by heating under reflux for 3 hours. The solvent was then evaporated under a reduced pressure, and the residue was purified by silica gel chromatography (eluant: n-hexane/ethyl acetate=2/1) to give 0.3 g of the title compound (colorless crystals).

Example 11

N-methoxymethyl -7-(2-chloro-6-fhoro-4-trifluoromethylphenoxy)-2,4-dimethyl-3,4,dihydro-3-oxo-2H-1,4-benzoxazine-2-carboxvamide (Compound 72)

7-(2-Chloro-6-fluoro-4-trifluoromethylphenoxy)-2,4-dimethyl-3,4-dihydro-3-oxo-2H-1,4-benzoxazine-2-carboxyamide (Compound 55) (0.4 g) was dissolved in toluene (5 ml), chlorodimethyl ether (0.1 ml) and sodium hydride (0.1 g) were added thereto, and the mixture was stirred at room temperature for 2 hours. The reaction mixture was poured into ice-water, extracted twice with ethyl acetate (20 ml), and the extract was washed with water and then with saturated aqueous sodium chloride, and dried over magnesium sulfate, followed by an evaporation of the solvent under a reduced pressure. The residue was purified by silica gel chromatography (eluant: n-hexane/ethyl acetate=2/1) to give 0.3 g of the title compound (colorless oil).

Example 12

N-(2-ethoxycarbonylethyl)-7-(2-chloro-6-fluoro-4-trifluoromethylphenoxy)-2,4-dimethyl-3,4-dihydro-3-oxo-2H-1,4-benzoxazine-2-carboxyamide (Compound 76)

βAlanine ethyl ester hydrochloride was dissolved in methylene chloride (5 ml), and a methylene chloride (5 ml) solution of an acid chloride (0.5 g) obtained as in Example 6 from triethylamine (0.4 ml) and 7-(2-chloro-6-fluoro-4-trifluoromethylphenoxy)-2,4-dimethyl-3,4-dihydro-3-oxo-2H-1,4-benzoxazine-2-carboxylic acid (Compound 25) was added thereto, followed by stirring at room temperature for 2 hours. The reaction mixture was then concentrated under a reduced pressure, and the residue was extracted twice with ethyl acetate (20 ml). The extract was successively washed with 1N-hydrochloric acid, water, saturated aqueous sodium bicarbonate, saturated aqueous sodium chloride, and then dried over magnesium sulfate. The solvent was then evaporated under a reduced pressure, and the residue purified by silica gel chromatography (eluant: n-hexane/ethyl acetate=1/1) to give 0.4 g of the title compound (colorless oil).

Example 13

7-(2-Chloro-6-fluoro-4-trifluoromethylphenoxy)-2,4-dimethyl-2-propionyl-3,4-dihydro-3-oxo-2H-1,4-benzoxazine (Compound 87) and
7-(2-Chloro-6-fluoro-4-trifluoromethylphenoxy)-2,4-dimethyl-2-[3-(3-hydroxypentyl)]-3,4-dihydro-3-oxo-2H-1,4-benzoxazine (Compound 88)

An acid chloride (0.8 g) obtained as in Example 6 from 7-(2-chloro-6-fluoro-4-trifluoromethylphenoxy)-2,4-dimethyl-3,4-dihydro-3-oxo-2H-1,4-benzoxazine-2-carboxylic acid (Compound 25) was dissolved in THF (5 ml), cooled in a dry ice-acetone bath under nitrogen gas atmosphere, and then 1M-ethyl magnesium bromide THF solution (1.9 ml) was dropwise added thereto over 5 minutes. After stirring at room temperature overnight, water was added to the reaction mixture, the mixture was extracted twice with ethyl acetate (20 ml), and the extract was washed with water and then with saturated aqueous sodium chloride, and dried over magnesium sulfate. The solvent was then evaporated under a reduced pressure, and the residue was purified by separation by silica gel chromatography (eluant: n-hexane/ethyl acetate=3/1) to give 0.3 g and 0.2 g respectively of the two title compounds (colorless crystals).

Example 14

7-(2-Chloro-6-fluoro-4-trifluoromethylphenoxy)-2,4-dimethyl-2-diazoacetyl-3,4-dihydro-3-oxo-2H-1,4-benzoxazine (Compound 91)

To a diazomethane ether solution (250 ml) prepared in conventional manner was added, under ice-cooling, a THF (5 ml) solution of an acid chloride (3.0 g) obtained as in Example 6 from 7-(2-chloro-6-fluoro-4-trifluoromethylphenoxy)-2,4-dimethyl-3,4-dihydro-3-oxo-2H-1,4-benzoxazine-2-carboxylic acid (Compound 25) and the mixture was stirred at room temperature for 10 minutes. The reaction mixture was then concentrated under a reduced pressure, and the residue purified by silica gel chromatography (ehant: n-hexane/ethyl acetate=3/1) to give 2.8 g of the title compound (colorless crystals).

Example 15

7-12-Chloro-6-fhoro-4-trifhoromethylphenoxy)-2,4-dimethyl-2-acetyl-3,4,dihydro-3-oxo-2H-1,4-benzoxazine (Compound 93)

Under ice-cooling, 55% hydroiodic acid (1 ml) was added to an ether (10 ml) solution of 7-(2-chloro-6-fluoro-4-trifluoromethylphenoxy)-2,4-dimethyl-2-diazoacetyl-3,4-dihydro-3-oxo-2H-1,4-benzoxazine (Compound 91) (1.8 g) obtained in Example 14, and the mixture was stirred for 30 minutes. The reaction mixture was washed with water and then dried over magnesium sulfate, followed by concentration under a reduced pressure. The residue was then purified by silica gel chromatography (ehant: n-hexane/ethyl acetate=2/1) to give 0.4 g of the title compound (colorless crystals).

In Example 15, dichloromethane was used as the solvent, and trifluoroacetic acid or conc. hydrochloric acid was used in place of hydroiodic acid, and 7-(2-chloro-6-fluoro-4-trifluoromethylphenoxy)-2,4-dimethyl-2-hydroxyacetyl-3,4-dihydro-3-oxo-2H-1,4-benzoxazine (Compound 95) and 7-(2-chloro-6-fluoro-4-trifluoromethylphenoxy)-2,4-dimethyl-2-chloroacetyl-3,4-dihydro-3-oxo-2H-1,4-benzoxazine (Compound 97) were obtained.

Example 16

7-(2-Chloro-6-fluoro-4-trifluoromethylphenoxy)-2,4-dimethyl-2-[1-(hydroxyimino)ethyl]-3,4-dihydro-3-oxo-2H-1,4-benzoxazine (Compound 101)

7-(2-Chloro-6-fluoro-4-trifluoromethylphenoxy)-2,4-dimethyl-2-acetyl-3,4-dihydro-3-oxo-2H-1,4-benzoxazine (Compound 93) (0.3 g) obtained in Example 15 was dissolved in ethanol (10 ml), and hydroxylamine hydrochloride (0.1 g) and 1N-sodium hydroxide (0.8 ml) were added, followed by stirring at 90° C. for 2 hours. The reaction mixture was concentrated under a reduced pressure, and the residue was purified by silica gel chromatography (eluant: n-hexane/ethyl acetate=2/1) to give 0.3 g of the title compound (colorless crystals).

Example 17

7-(2-Chloro-6-fluoro-4-trifluoromethylphenoxy)-2,4-dimethyl-2-[1-(methoxyimino)ethy]-3,4-dihydro-3-oxo-2H-1,4-benzoxazine (Compound 102)

7-(2-Chloro-6-fluoro-4-trifluoromethylphenoxy)-2,4-dimethyl-2-acetyl-3,4-dihydro-3-oxo-2H-1,4-benzoxazine (Compound 93) (0.3 g) obtained in Example 15 was dissolved in pyridine (4 ml), o-methylhydroxylamine hydrochloride (0.1 g) was added, and the mixture was stirred at room temperature for 4 hours, and further, at 60° C. for one hour. The reaction mixture was then poured into ice-water, and the mixture was extracted twice with ethyl acetate (20 ml). The extract was washed with 1N-hydrochloric acid and then with saturated aqueous sodium chloride, and dried over magnesium sulfate. The solvent was evaporated under a reduced pressure, and the residue was purified by silica gel chromatography (eluant: n-hexane/ethyl acetate=4/1) to give 0.3 g of the title compound (colorless oil).

Example 18

7-(2-Chloro-6-fluoro-4-trifluoromethylphenoxy)-2,4-dimethyl-2-[1-(ethoxyimino)ethyl]-3,4-dihydro-3-oxo-2H-1,4-benzoxazine (Compound 104)

To a DMF (10 ml) solution of 7-(2-chloro-6-fluoro-4-trifluoromethylphenoxy)-2,4-dimethyl-2-[1(hydroxyimino)ethyl]-3,4-dihydro-3-oxo-2H-1,4-benzoxazine (Compound 101) (0.3 g) obtained in Example 16 was added, under ice-cooling, 60% sodium hydride (0.03 g), and after stirring for 20 minutes, bromoethane (0.1 g) was dropwise added thereto. After stirring for 2 hours, 1N hydrochloric acid was added and the mixture extracted twice with ethyl acetate (20 ml). The extract was then washed with water and with saturated aqueous sodium chloride, and dried over magnesium sulfate. The solvent was evaporated under a reduced pressure, and the residue purified by silica gel chromatography (eluant: n-hexane/ethyl acetate=4/1) to give 0.3 g of the title compound (colorless oil).

The above-prepared compounds of the Examples and other compounds, which could be prepared by using any one of the methods shown in Examples 1 to 18, are shown, together with their physical properties, in Table 1 (in the table, * shows the position of substitution).

TABLE 1

[Structure: F$_3$C substituted pyridine/benzene ring (A) with Cl, connected via O* to a benzene ring bearing N(R$^1$) and a fused ring containing Z, R$^2$, R$^3$, and O]

| Compound No. | A | * | Z | R$^1$ | R$^2$ | R$^3$ | Physical properties |
|---|---|---|---|---|---|---|---|
| 1 | C—H | 7 | O | H | H | COOEt | m.p. 180.5–182.0° C. |
| 5 | N | 6 | O | H | H | COOEt | m.p. 190.0–191.0° C. |
| 2 | C—H | 7 | O | H | Me | COOEt | m.p. 112.0–113.5° C. |
| 3 | C—Cl | 7 | O | H | Me | COOEt | m.p. 116.0–118.0° C. |
| 4 | C—F | 7 | O | H | Me | COOEt | m.p. 109.0–111.0° C. |
| 6 | C—H | 7 | O | Me | H | COOEt | oily n$_D^{25}$ 1.49435 |
| 7 | C—H | 7 | O | Me | Me | COOEt | m.p. 86.0–88.0° C. |
| 8 | C—H | 7 | O | Et | Et | COOEt | oily n$_D^{25}$ 1.48855 |
| 9 | C—H | 7 | O | n-Pr | Me | COOEt | oily n$_D^{25}$ 1.48415 |
| 10 | C—H | 7 | O | i-Pr | Me | COOEt | m.p. 65.0–67.0° C. |
| 11 | C—H | 7 | O | CH$_2$C≡CH | Me | COOEt | oily n$_D^{25}$ 1.49700 |
| 12 | C—H | 7 | O | Bzl | Me | COOEt | oily n$_D^{25}$ 1.47900 |
| 13 | C—H | 7 | O | CH$_2$OMe | Me | COOEt | oily n$_D^{25}$ 1.46370 |
| 14 | C—H | 7 | O | Ac | Me | COOEt | oily n$_D^{25}$ 1.47480 |
| 15 | C—H | 7 | O | Et | Et | COOEt | oily n$_D^{25}$ 1.47555 |
| 16 | C—Cl | 7 | O | Me | Me | COOEt | m.p. 90.0–92.0° C. |
| 17 | C—F | 7 | O | Me | Me | COOEt | m.p. 105.0–105.5° C. |
| 18 | N | 6 | O | Me | H | COOEt | m.p. 81.0–83.0° C. |
| 19 | N | 6 | O | Me | Me | COOEt | oily n$_D^{25}$ 1.46480 |
| 20 | C—Cl | 7 | O | CHF$_2$ | Me | COOEt | oily n$_D^{25}$ 1.49240 |
| 21 | C—H | 7 | S | H | H | C(=S)OEt | m.p. 130.0–132.0° C. |
| 22 | C—H | 7 | S | Me | Me | C(=S)OEt | oily n$_D^{25}$ 1.54915 |
| 23 | C—H | 7 | O | Me | Me | COOH | m.p. 50.0–52.0° C. |
| 24 | C—Cl | 7 | O | Me | Me | COOH | m.p. 171.0–172.0° C. |
| 25 | C—F | 7 | O | Me | Me | COOH | m.p. 162.0–163.0° C. |
| 26 | C—H | 7 | O | Me | Me | COONa | m.p. 172.5–173.5° C. |
| 27 | C—H | 7 | O | Me | Me | COOK | m.p. 207.0–209.0° C. |
| 28 | C—F | 7 | O | Me | Me | COONa | m.p. 211.5–213.5° C. |
| 29 | C—H | 7 | O | Me | Me | COOMe | m.p. 107.0–108.0° C. |
| 30 | C—H | 7 | O | Me | Me | COOPr | m.p. 64.0–66.0° C. |
| 31 | C—H | 7 | O | Me | Me | COOi-Pr | m.p. 89.0–91.0° C. |
| 32 | C—H | 7 | O | Me | Me | COOBu | m.p. 75.5–76.5° C. |
| 33 | C—H | 7 | O | Me | Me | COOt-Bu | oily n$_D^{25}$ 1.47755 |
| 34 | C—H | 7 | O | Me | Me | COOPh(p-Cl) | oily n$_D^{25}$ 1.49120 |
| 35 | C—H | 7 | O | Me | Me | COOBzl | m.p. 77.5–79.5° C. |
| 36 | C—H | 7 | O | Me | Me | COOCH$_2$COCH$_3$ | m.p. 122.5–124.5° C. |
| 37 | C—H | 7 | O | Me | Me | COOCH$_2$CH$_2$OMe | oily n$_D^{25}$ 1.49295 |
| 38 | C—H | 7 | O | Me | Me | C(=O)SEt | oily n$_D^{25}$ 1.46550 |
| 39 | C—Cl | 7 | O | Me | Me | COOPr | m.p. 95.0–96.5° C. |
| 40 | C—Cl | 7 | O | Me | Me | COOCH$_2$CH$_2$OMe | oily n$_D^{25}$ 1.45880 |
| 41 | C—Cl | 7 | O | Me | Me | COOCH$_2$CH=CH$_2$ | m.p. 121.0–123.0° C. |
| 42 | C—F | 7 | O | Me | Me | COOPr | oily n$_D^{25}$ 1.45175 |
| 43 | C—F | 7 | O | Me | Me | COOCH$_2$CH=CH$_2$ | oily n$_D^{25}$ 1.46955 |
| 44 | C—F | 7 | O | Me | Me | COOCH$_2$C≡CH | m.p. 100.0–102.0° C. |
| 45 | C—F | 7 | O | Me | Me | COOCH$_2$CF$_3$ | oily n$_D^{25}$ 1.47200 |
| 46 | C—H | 7 | O | Me | Me | COOCH$_2$CO$_2$Me | m.p. 62.0–64.0° C. |
| 47 | C—F | 7 | O | Me | Me | COOCH$_2$CON(H)Et | oily n$_D^{25}$ 1.44930 |
| 48 | C—H | 7 | O | Me | Me | CONH$_2$ | m.p. 151.0–152.5° C. |
| 49 | C—H | 7 | O | Me | Me | CON(H)Et | m.p. 124.0–125.0° C. |
| 50 | C—H | 7 | O | Me | Me | CON(Me)OMe | m.p. 148.5–149.5° C. |
| 51 | C—H | 7 | O | Me | Me | CON(Et)$_2$ | oily n$_D^{25}$ 1.43725 |
| 52 | C—H | 7 | O | Me | Me | CON(H)Pyrimidine-2-yl(4,6-di-Me) | m.p. 164.0–165.0° C. |
| 53 | C—Cl | 7 | O | Me | Me | CON(H)Et | m.p. 148.5–150.5° C. |
| 54 | C—Cl | 7 | O | Me | Me | CON(H)CH$_2$CH=CH$_2$ | m.p. 155.0–157.0° C. |
| 55 | C—F | 7 | O | Me | Me | CONH$_2$ | m.p. 145.0–146.0° C. |
| 56 | C—F | 7 | O | Me | Me | CON(H)Me | m.p. 148.0–150.0° C. |
| 57 | C—F | 7 | O | Me | Me | CON(H)Et | m.p. 58.0–60.0° C. |
| 58 | C—F | 7 | O | CHF$_2$ | Me | CON(H)Et | m.p. 158.5–160.5° C. |
| 59 | C—F | 7 | O | Me | Me | CON(H)Pr | oily n$_D^{25}$ 1.46600 |
| 60 | C—F | 7 | O | Me | Me | CON(H)i-Pr | m.p. 141.0–142.0° C. |
| 61 | C—F | 7 | O | Me | Me | CON(H)Bu | oily n$_D^{25}$ 1.48620 |
| 62 | C—F | 7 | O | Me | Me | CON(H)cyclohexyl | m.p. 124.5–126.5° C. |
| 63 | C—F | 7 | O | Me | Me | CON(H)octyl | m.p. 95.0–97.0° C. |
| 64 | C—F | 7 | O | Me | Me | CON(H)Bzl | oily n$_D^{25}$ 1.45205 |
| 65 | C—F | 7 | O | Me | Me | CON(H)CH$_2$CH=CH$_2$ | oily n$_D^{25}$ 1.45925 |
| 66 | C—F | 7 | O | Me | Me | CON(H)CH$_2$C≡CH | m.p. 143.5–145.5° C. |
| 67 | C—F | 7 | O | Me | Me | CON(H)CH$_2$CH$_2$Cl | oily n$_D^{25}$ 1.52840 |
| 68 | C—F | 7 | O | Me | Me | CON(H)CH$_2$CF$_3$ | m.p. 180.0–181.0° C. |

TABLE 1-continued

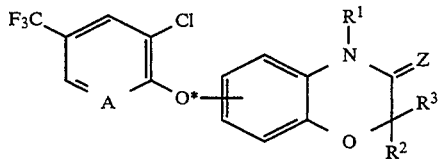

| Compound No. | A | * | Z | $R^1$ | $R^2$ | $R^3$ | Physical properties |
|---|---|---|---|---|---|---|---|
| 69 | C—F | 7 | O | Me | Me | CON(H)Ph(p-Cl) | oily $n_D^{25}$ 1.52760 |
| 70 | C—F | 7 | O | Me | Me | CON(H)OMe | m.p. 75.0–77.0° C. |
| 71 | C—F | 7 | O | Me | Me | CON(H)CH$_2$CH$_2$OMe | oily $n_D^{25}$ 1.50380 |
| 72 | C—F | 7 | O | Me | Me | CON(H)CH$_2$OMe | m.p. 126.0–128.0° C. |
| 73 | C—F | 7 | O | Me | Me | CON(Me)$_2$ | m.p. 212.0–213.0° C. |
| 74 | C—F | 7 | O | Me | Me | CON(H)CO$_2$Et | m.p. 182.0–183.0° C. |
| 75 | C—F | 7 | O | Me | Me | CON(H)CH$_2$CO$_2$Et | m.p. 47.0–49.0° C. |
| 76 | C—F | 7 | O | Me | Me | CON(H)CH$_2$CH$_2$CO$_2$Et | m.p. 60.0–62.0° C. |
| 77 | C—F | 7 | O | Me | Me | CON(H)CH(CH$_3$)CO$_2$Et | oily $n_D^{25}$ 1.52045 |
| 78 | C—F | 7 | O | Me | Me | CON(H)CH$_2$CO$_2$H | m.p. 59.0–61.0° C. |
| 79 | C—F | 7 | O | Me | Me | CON(H)CH$_2$(CH$_3$)CON(H)Et | m.p. 82.0–84.0° C. |
| 80 | C—F | 7 | O | Me | Me | CON(H)Ac | oily $n_D^{25}$ 1.49480 |
| 81 | C—F | 7 | O | Me | Me | CON(H)COCH$_2$CH$_3$ | m.p. 51.0–53.0° C. |
| 82 | C—F | 7 | O | Me | Me | CON(H)SO$_2$CH$_3$ | m.p. 110.0–112.0° C. |
| 83 | C—F | 7 | O | Me | Me | CON(H)CON(H)Et | m.p. 198.0–199.5° C. |
| 84 | C—F | 7 | O | Me | Me | CON(H)C(=S)N(H)Et | m.p. 156.5–158.0° C. |
| 85 | C—F | 7 | O | Me | Me | CON(H)C(=S)OEt | glassy |
| 86 | C—F | 7 | O | Me | Me | CON(H)N(Me)$_2$ | m.p. 121.0–122.0° C. |
| 87 | C—F | 7 | O | Me | Me | C(=O)Et | m.p. 112.0–114.0° C. |
| 88 | C—F | 7 | O | Me | Me | C(Et)$_2$OH | m.p. 109.0–110.0° C. |
| 89 | C—F | 7 | O | Me | Me | C(=O)Pr | m.p. 107.5–108.5° C. |
| 90 | C—F | 7 | O | Me | Me | C(=O)Bu | oily $n_D^{25}$ 1.48070 |
| 91 | C—F | 7 | O | Me | Me | C(=O)CHN$_2$ | m.p. 133.5–134.5° C. |
| 92 | C=Cl | 7 | O | Me | Me | C(=O)CHN$_2$ | m.p. 138.5–139.5° C. |
| 93 | C—F | 7 | O | Me | Me | C(=O)Me | m.p. 117.0–118.5° C. |
| 94 | C—Cl | 7 | O | Me | Me | C(=O)Me | m.p. 104.0–106.0° C. |
| 95 | C—F | 7 | O | Me | Me | C(=O)CH$_2$OH | glassy |
| 96 | C—Cl | 7 | O | Me | Me | C(=O)CH$_2$OH | m.p. 160.0–162.0° C. |
| 97 | C—F | 7 | O | Me | Me | C(=O)CH$_2$Cl | m.p. 123.0–125.0° C. |
| 98 | C—F | 7 | O | Me | Me | C(=O)CH$_2$Br | m.p. 109.0–110.0° C. |
| 99 | C—F | 7 | O | Me | Me | C(=O)CH$_2$OAc | oily $n_D^{25}$ 1.47755 |
| 100 | C—F | 7 | O | Me | Me | C(=O)CH$_2$OC(=O)CH$_2$OAc | glassy |
| 101 | C—F | 7 | O | Me | Me | C(=NOH)Me | m.p. 69.0–71.0° C. |
| 102 | C—F | 7 | O | Me | Me | C(=NOMe)Me | oily $n_D^{25}$ 1.46380 |
| 103 | C—Cl | 7 | O | Me | Me | C(=NOMe)Me | oily $n_D^{25}$ 1.46900 |
| 104 | C—F | 7 | O | Me | Me | C(=NOEt)Me | oily $n_D^{25}$ 1.47225 |
| 105 | C—Cl | 7 | O | Me | Me | C(=NOi-Pr)Me | oily $n_D$ 1.44420 |
| 106 | C—F | 7 | O | Me | Me | C(=NOCH$_2$CH=CH$_2$)Me | oily $n_D^{25}$ 1.47860 |
| 107 | C—Cl | 7 | O | Me | Me | C(=NOCH$_2$CH=CH)Me | oily $n_D^{25}$ 1.48445 |
| 108 | C—F | 7 | O | Me | Me | C(=NOCH$_2$C≡CH)Me | oily $n_D^{25}$ 1.47195 |
| 109 | C—Cl | 7 | O | Me | Me | C[=NOCH(Me)CO$_2$Et]Me | m.p. 52.0–54.0° C. |
| 110 | C—F | 7 | O | Me | Me | C[=N—N(H)Me]Me | m.p. 123.0–125.0° C. |
| 111 | C—F | 7 | O | Me | H | C(O—CH$_2$—)$_2$Me | oily $n_D^{25}$ 1.48320 |

Reference Example 1

Diethyl 2-[5-(2-chloro-4-trifluoromethylphenoxy)-2-nitrophenoxy]malonate (IV=1)

To a suspension of 60% sodium hydride (0.4 g) in DMF (5 ml) was dropwise added, under ice-cooling, a DMF (5 ml) solution of 5-(2-chloro-4-trifluoromethylphenoxy)-2-nitrophenol (3.3 g), and the mixture was stirred for 10 minutes. To the solution was added diethyl bromomalonate (2.1 ml), and the mixture stirred at 70° C. for 30 minutes. Then, to the reaction mixture was added water (10 ml), and the mixture extracted twice with ethyl acetate (20 ml). The extract was washed with water and then with saturated aqueous sodium chloride, and dried over magnesium sulfate. The solvent was evaporated under a reduced pressure, and the residue was purified by silica gel chromatography (eluant: n-hexane/ethyl acetate=5/1) to give 3.0 g of the title compound (colorless oil). Also, 0.7 g of the phenol derivative of the starting material was recovered.

NMR (δppm, CDCl$_3$): 1.29 (6H, t, J=8 Hz), 4.30 (4H, q, J=8 Hz), 5.16 (1H, s), 6.56–6.68 (2H, m), 7.20 (1H, d, J=9 Hz), 7.59 (1H, dd, J=9 & 2 Hz), 7.77 (1H, d, J=2 Hz), 7.97 (1H, d, J=10 Hz)

In Reference Example 1, by carrying out the reaction in the same manner, but using 4-(3-chloro-5-trifluoromethylpyridin-2-yloxy)-2-nitrophenol in place of 5-(2-chloro-4-trifluoromethylphenoxy)-2-nitrophenol, diethyl 2-[4-(3-chloro-5-trifluoromethylpyridin-2-yloxy)-2-nitrophenoxy]malonate (IV-5) was obtained.

Similarly by using diethyl bromomethylmalonate in place of diethyl bromomalonate, and carrying out the reaction with 5-(2-chloro-4-trifluoromethylphenoxy)-2-nitrophenol, 5-(2,6-dichloro-4-trifluoromethylphenoxy)-2-nitrophenol or 5-(2-chloro-6-fluoro-4-trifluoromethylphenoxy)-2-nitrophenol, diethyl 2-[5-(2-chloro-4-trifluoromethylphenoxy)-2-nitrophenoxy]-2-methylmalonate (IV-2), diethyl 2-[5-(2,6-dichloro-4-trifluoromethylphenoxy)-2-nitrophenxoy]-2-methylmalonate (IV-3) and diethyl 2-[5-(2-chloro-6-fluoro-4-trifluoromethylphenoxy)-2-nitrophenoxy]-2-methylmalonate (IV-4) were obtained. The physical properties of these compounds are shown in Table 2.

TABLE 2

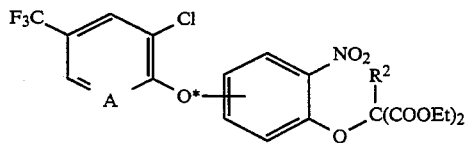

| Compound No. | A | * | $R^2$ | Physical properties |
|---|---|---|---|---|
| IV-2 | C—H | 5 | Me | oily substance $n_D^{25}$ 1.45575 |
| IV-3 | C—Cl | 5 | Me | oily substance $n_D^{25}$ 1.47855 |
| IV-4 | C—F | 5 | Me | oily substance $n_D^{25}$ 1.48175 |
| IV-5 | N | 4 | H | m.p. 36.5–38.5° C. |

Test Example 1 (Soil treatment)

Seeds of large-crab grass (*Digitaria adscendens* Henr.), barnyardgrass (Penicum Crus-galli), purslane (*Portulaca oleracea*), smartweed (Polygonum blumei Meisn.) and umbrella plant (*Cyperus microiria*) were planted in a seedling case, having a size of 6 cm×15 cm×10 cm, packed with soil. On the day following the seeding, the test compounds in the form of a 20% wettable powder were diluted with 200 liters of water per 10 a, and sprayed onto the surface of the soil, so that the dosage of the test compounds was 400 g or 50 g per 10 a, in terms of the active ingredient. Two weeks after the treatment with the test compounds, the herbicidal activity was measured by visible observation (5: completely dead - 0: no herbicidal activity). The results are shown in Table 3.

TABLE 3

| Compound No. | Field - soil treatment - | | | | | | | | | |
|---|---|---|---|---|---|---|---|---|---|---|
| | Large crabgrass | | *Penicum Crusgalli* | | Purslane | | Smartweed | | Umbrella plant | |
| | 400 g | 50 g | 400 g | 50 g | 400 g | 50 g | 400 g | 50 g | 400 g | 50 g |
| 9 | 3 | | 5 | | 5 | | 4 | | 5 | |
| 12 | 2.5 | | 5 | | 5 | | 2.5 | | 4 | |
| 16 | 5 | | 5 | | 5 | | 5 | | 5 | |
| 18 | | 5 | | 5 | | 5 | | 2.5 | | 4 |
| 25 | 5 | | 5 | | 5 | | 5 | | 5 | |
| 28 | 5 | | 5 | | 5 | | 5 | | 5 | |
| 30 | 4.5 | | 5 | | 5 | | 5 | | 5 | |
| 37 | | 5 | | 5 | | 5 | | 5 | | 5 |
| 43 | | 3 | | 5 | | 4.5 | | 2 | | 5 |
| 44 | | 2 | | 2.5 | | 3.5 | | 2 | | 4 |
| 45 | | 3 | | 4 | | 3 | | 3.5 | | 5 |
| 47 | | 2.5 | | 4.5 | | 5 | | 4.5 | | 4.5 |
| 50 | 1 | | 5 | | 5 | | 5 | | 5 | |
| 53 | | 5 | | 5 | | 5 | | 5 | | 5 |
| 54 | | 4.5 | | 5 | | 5 | | 5 | | 5 |
| 55 | 5 | | 5 | | 5 | | 5 | | 5 | |
| 56 | 5 | | 5 | | 5 | | 5 | | 5 | |
| 57 | | 5 | | 5 | | 5 | | 5 | | 5 |
| 58 | | 2 | | 5 | | 5 | | 5 | | 5 |
| 59 | | 3 | | 5 | | 5 | | 5 | | 5 |
| 67 | | 3 | | 5 | | 5 | | 5 | | 5 |
| 71 | | 3.5 | | 5 | | 5 | | 3 | | 5 |
| 72 | | 5 | | 5 | | 5 | | 4.5 | | 5 |
| 75 | | 3 | | 4.5 | | 5 | | 4.5 | | 4 |
| 76 | | 4.5 | | 4.5 | | 5 | | 5 | | 4.5 |
| 78 | | 3 | | 3.5 | | 4.5 | | 4 | | 3 |
| 81 | | 2.5 | | 3.5 | | 5 | | 5 | | 4.5 |
| 82 | | 4 | | 4.5 | | 5 | | 5 | | 4.5 |
| 86 | | 4 | | 5 | | 5 | | 5 | | 5 |
| 91 | | 3 | | 3 | | 3.5 | | 5 | | 4.5 |
| 93 | | 2.5 | | 4.5 | | 5 | | 3.5 | | 5 |
| 102 | | 1.5 | | 2.5 | | 5 | | 3 | | 5 |
| 110 | | 2.5 | | 4.5 | | 5 | | 4.5 | | 5 |
| 111 | | 2.5 | | 3.5 | | 5 | | 4.5 | | 5 |

Test Example 2 (Foilage treatment)

Seeds of large-crab grass ( Digitaria adscendens Henr.), barnyardgrass (Penicum Crus-galli), purslane (*Portulaca oleracea*), smartweed (Polygonum blumei Meisn.) and umbrella plant (*Cyperus microiria*) were planted in a seedling case, having a size of 6 cm×15 cm×10 cm, packed with soil. After 10 day's growth in a green house, the test compounds in the form of a 20% wettable powder were diluted to 200 liters per 10 a, and sprayed onto the surface of the foliage, so that the dosage of the test compounds was 400 g or 50 g, in terms of the active ingredient. Two weeks after the treatment with the test compounds, the herbicidal activity was measured by visual observation (5: completely dead - 0: no herbicidal activity). The results are shown in Table 4.

TABLE 4

| Compound No. | Field - foliage treatment - | | | | | | | | | |
|---|---|---|---|---|---|---|---|---|---|---|
| | Large crabgrass | | *Penicum Crus-galli* | | Purslane | | Smartweed | | Umbrella plant | |
| | 400 g | 50 g | 400 g | 50 g | 400 g | 50 g | 400 g | 50 g | 400 g | 50 g |
| 9 | 4.5 | | 5 | | 5 | | 5 | | 5 | |
| 12 | 3 | | 5 | | 5 | | 4.5 | | 3 | |
| 16 | 5 | | 5 | | 5 | | 5 | | 5 | |

TABLE 4-continued

| Compound No. | Field · foliage treatment - | | | | | | | | | |
|---|---|---|---|---|---|---|---|---|---|---|
| | Large crabgrass | | *Penicum Crus-galli* | | Purslane | | Smartweed | | Umbrella plant | |
| | 400 g | 50 g | 400 g | 50 g | 400 g | 50 g | 400 g | 50 g | 400 g | 50 g |
| 18 | | 5 | | 5 | | 5 | | 2.5 | | 4 |
| 25 | 5 | | 5 | | 5 | | 5 | | 5 | |
| 28 | 5 | | 5 | | 5 | | 5 | | 5 | |
| 30 | 4.5 | | 5 | | 5 | | 5 | | 5 | |
| 37 | | 4 | | 5 | | 5 | | 5 | | 5 |
| 43 | | 4 | | 5 | | 5 | | 5 | | 5 |
| 44 | | 1.5 | | 4.5 | | 5 | | 5 | | 3.5 |
| 45 | | 4.5 | | 5 | | 5 | | 5 | | 5 |
| 47 | | 2.5 | | 4.5 | | 5 | | 4.5 | | 4.5 |
| 50 | 2 | | 5 | | 5 | | 2.5 | | 5 | |
| 53 | | 2.5 | | 5 | | 5 | | 5 | | 4.5 |
| 54 | | 1 | | 5 | | 5 | | 4 | | 4 |
| 55 | 5 | | 5 | | 5 | | 5 | | 5 | |
| 56 | | 5 | | 5 | | 5 | | 5 | | 5 |
| 57 | | 4.5 | | 5 | | 5 | | 5 | | 5 |
| 58 | | 1 | | 5 | | 5 | | 2.5 | | 2.5 |
| 59 | | 2.5 | | 5 | | 5 | | 5 | | 5 |
| 67 | | 2 | | 5 | | 5 | | 5 | | 5 |
| 71 | | 5 | | 5 | | 5 | | 5 | | 5 |
| 72 | | 5 | | 5 | | 5 | | 5 | | 5 |
| 75 | | 5 | | 5 | | 5 | | 5 | | 5 |
| 76 | | 5 | | 5 | | 5 | | 4.5 | | 4.5 |
| 78 | | 5 | | 5 | | 5 | | 5 | | 5 |
| 81 | | 3 | | 5 | | 5 | | 5 | | 5 |
| 82 | | 5 | | 5 | | 5 | | 4.5 | | 5 |
| 86 | | 3 | | 5 | | 5 | | 5 | | 5 |
| 91 | | 2 | | 5 | | 5 | | 4.5 | | 5 |
| 93 | | 2 | | 4.5 | | 5 | | 5 | | 4 |
| 102 | | 2 | | 5 | | 5 | | 5 | | 2.5 |
| 110 | | 2.5 | | 5 | | 5 | | 5 | | 4.5 |
| 111 | | 2.5 | | 4 | | 5 | | 5 | | 4 |

Test Example 3 (Soil treatment)

Seeds of barnyardgrass (Echinocloa Oryjicola), monochoria (*Monochoria vaginalis*), small flower umbrella plant (*Cyperus difformis*), Ammannia multiflora Roxb. and Scirupus hotarui were planted in a polyvinyl chloride pack, having a size of 6 cm×16 cm×11 cm, packed with soil and filled with water. On the day following the seeding, the test compounds in the form of an acetone solution (in some cases ethanol or an aqueous solution) were diluted with 60 ml of water per one pack, and dropwise added to the water in the pack, so that the dosage of the test compounds was 400 g or 25 g per 10 a, in terms of the active ingredient. Four weeks after the treatment with the test compounds, the herbicidal activity was measured by visual observation (5: completely dead, - 0: no herbicidal activity). The results are shown in Table 5.

TABLE 5

| Compound No. | Paddy field · soil treatment - | | | | | | | | | |
|---|---|---|---|---|---|---|---|---|---|---|
| | *Echinocloa oryjicola* | | Monochoria | | Small flower umbrella plant | | Ammania multiflora Roxb. | | *Scirupus Hotarui* | |
| | 400 g | 25 g | 400 g | 25 g | 400 g | 25 g | 400 g | 25 g | 400 g | 25 g |
| 9 | 5 | | 5 | | 5 | | 5 | | 4 | |
| 12 | 5 | | 5 | | 5 | | 5 | | 4 | |
| 16 | 5 | | 5 | | 5 | | 5 | | 4 | |
| 18 | | 5 | | 5 | | 5 | | 5 | | 2 |
| 25 | 5 | | 5 | | 5 | | 5 | | 5 | |
| 28 | 5 | | 5 | | 5 | | 5 | | 5 | |
| 30 | 5 | | 5 | | 5 | | 5 | | 5 | |
| 37 | | 5 | | 5 | | 5 | | 5 | | 5 |
| 39 | | 5 | | 5 | | 5 | | 5 | | 3 |
| 43 | | 5 | | 5 | | 5 | | 5 | | 5 |
| 44 | | 5 | | 5 | | 5 | | 5 | | 4 |
| 45 | | 5 | | 5 | | 5 | | 5 | | 5 |
| 47 | | 5 | | 5 | | 4 | | 5 | | 2 |
| 50 | 5 | | 5 | | 5 | | 5 | | 3 | |
| 53 | | 5 | | 5 | | 5 | | 5 | | 3 |
| 55 | 5 | | 5 | | 5 | | 5 | | 5 | |
| 56 | | 5 | | 5 | | 5 | | 5 | | 4 |
| 57 | | 5 | | 5 | | 5 | | 5 | | 4.5 |
| 61 | | 5 | | 5 | | 5 | | 5 | | 2 |
| 67 | | 5 | | 5 | | 5 | | 5 | | 2 |
| 71 | | 5 | | 5 | | 5 | | 5 | | 3 |
| 72 | | 5 | | 5 | | 5 | | 5 | | 3 |
| 75 | | 5 | | 5 | | 5 | | 5 | | 1 |
| 76 | | 5 | | 5 | | 5 | | 5 | | 3 |

TABLE 5-continued

| Compound No. | Paddy field - soil treatment - | | | | | | | | | |
|---|---|---|---|---|---|---|---|---|---|---|
| | Echinocloa oryjicola | | Monochoria | | Small flower umbrella plant | | Ammania multiflora Roxb. | | Scirupus Hotarui | |
| | 400 g | 25 g | 400 g | 25 g | 400 g | 25 g | 400 g | 25 g | 400 g | 25 g |
| 82 | | 5 | | 5 | | 5 | | 5 | | 2 |
| 85 | | 5 | | 5 | | 5 | | 5 | | 3 |
| 91 | | 5 | | 5 | | 5 | | 5 | | 0 |
| 93 | | 5 | | 5 | | 5 | | 5 | | 3 |
| 102 | | 5 | | 5 | | 5 | | 5 | | 2 |
| 110 | | 5 | | 5 | | 5 | | 5 | | 1.5 |
| 111 | | 5 | | 5 | | 5 | | 5 | | 2 |

Test Example 4 (Foilage treatment)

Seeds of barnyardgrass (Echinocloa Oryjicola), monochoria (*Monochoria vaginalis*), small flower umbrella plant (*Cyperus difformis*), Ammannia multiflora Roxb. and Scirupus hotarui were planted in a polyvinyl chloride pack, having a size of 6 cm×16 cm×1 cm, packed with soil and filled with water. After growth for about 2 weeks in a greenhouse, the test compounds in the form of an acetone solution (in some cases ethanol or aqueous solution) were diluted with 60 ml of water per one pack, and sprayed onto the surface of the foliage, so that the dosage of the test compounds was 400 g or 25 g per 10 a, in terms of the active ingredient. Three weeks after the treatment with the test compounds, the herbicidal activity was measured by visual observation (5: completely dead, - 0: no herbicidal activity). The results are shown in Table 6.

used before or after germination, either alone or as a combined drug produced by various preparations.

When applying the compound of the present invention as a herbicide, in general it can be applied by mixing with conventional carriers, for example, solid carriers such as clay or diatomaceous earth, liquid carriers such as water, alcohols, aromatic hydrocarbons, ethers, ketones or esters, etc., and if necessary or desired, it can be used with an addition of emulsifiers, dispersing agents, suspending agents, spreaders, and stabilizers, etc., or mixed with other herbicides, pesticides, sterilizers, and plant growth controllers. The active ingredient content is preferably 1 to 90% by weight.

The herbicide of the present invention can be used as a soil treatment agent before germination or as a foliage treatment agent after germination, and the dosage thereof can be varied widely, although preferably it is within a range of 0.1 to 400 g per 10 are.

TABLE 6

| Compound No. | Paddy field - foliage treatment - | | | | | | | | | |
|---|---|---|---|---|---|---|---|---|---|---|
| | Echinocloa oryjicola | | Monochoria | | Small flower umbrella plant | | Ammania multiflora Roxb. | | Scirupus Hotarui | |
| | 400 g | 25 g | 400 g | 25 g | 400 g | 25 g | 400 g | 25 g | 400 g | 25 g |
| 9 | 5 | | 5 | | 5 | | 5 | | 4 | |
| 12 | 5 | | 5 | | 5 | | 5 | | 4 | |
| 18 | | 5 | | 5 | | 5 | | 5 | | 3 |
| 37 | | 5 | | 5 | | 5 | | 5 | | 5 |
| 39 | | 5 | | 4 | | 5 | | 5 | | 5 |
| 43 | | 5 | | 5 | | 5 | | 5 | | 5 |
| 44 | | 5 | | 5 | | 5 | | 5 | | 4 |
| 45 | | 5 | | 4 | | 5 | | 5 | | 4 |
| 47 | | 5 | | 5 | | 5 | | 5 | | 2 |
| 50 | 3 | | 4 | | 5 | | 5 | | 2 | |
| 53 | | 5 | | 4 | | 5 | | 5 | | 1 |
| 55 | 5 | | 5 | | 5 | | 5 | | 4 | |
| 56 | | 5 | | 5 | | 5 | | 5 | | 3 |
| 57 | | 5 | | 5 | | 5 | | 5 | | 4.5 |
| 61 | | 4 | | 3 | | 5 | | 5 | | 2 |
| 67 | | 4 | | 3 | | 5 | | 5 | | 2 |
| 71 | | 5 | | 3 | | 5 | | 5 | | 2 |
| 72 | | 5 | | 3 | | 5 | | 5 | | 2 |
| 75 | | 5 | | 5 | | 5 | | 5 | | 3 |
| 76 | | 5 | | 5 | | 5 | | 5 | | 4 |
| 82 | | 5 | | 4 | | 5 | | 5 | | 3 |
| 85 | | 3 | | 3 | | 5 | | 5 | | 2 |
| 91 | | 5 | | 3 | | 5 | | 4 | | 1 |
| 93 | | 5 | | 4 | | 5 | | 5 | | 2 |
| 102 | | 3 | | 2 | | 5 | | 5 | | 2 |
| 110 | | 2 | | 4 | | 5 | | 5 | | 3 |
| 111 | | 4 | | 4 | | 5 | | 5 | | 2 |

As apparent from Test Examples 1–4, the compound of the present invention exhibits an excellent herbicidal activity against various weeds before and after germination, and is a useful compound for the herbicide.

The herbicidal effect of the compound of the present invention represented by the formula (I) enables it to be Preparation Example 1 (Emulsion)

Using a conventional method, 15 parts by weight of the Compound 37, 65 parts by weight of xylene and 20 parts by weight of polyoxyethylene alkylallyl ether were mixed to form a uniform solution, and an emulsion containing 15% of the active ingredient was obtained.

Preparation Example 2 (Wettable powder)

Using a conventional method, 40 parts by weight of the Compound 56, 55 parts by weight of Zieglite, 2 parts by weight of sodium alkylbenzenesulfonate, and 3 parts by weight of polyoxyethylene alkylallyl ether were uniformly pulverized and mixed to obtain a wettable powder containing 40% of the active ingredient.

Preparation Example 3 (Powder)

Using a conventional method, 5 parts by weight of the Compound 82, 20 parts by weight of bentonite, 73 parts by weight of clay, and 2 parts by weight of sodium dodecylbenzenesulfonate were uniformly mixed and kneaded with about 20 parts by weight of water, by a kneader. The mixture was granulated through a granulator, dried, and formed into granules containing 5% of the active ingredient.

We claim:

1. A benzoxazine derivative having the formula (I) or a salt thereof:

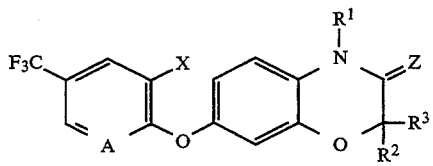

(I)

wherein A represents N or a CY group, where Y represents a hydrogen atom or a halogen atom;
X represents a chlorine atom;
Z represents an oxygen atom;
$R^1$ represents a lower alkyl group which may also be substituted with a halogen atom;
$R^2$ represents a hydrogen atom or a lower alkyl group;
$R^3$ represents a carboxyl group which may be esterified with a lower alkanol, a lower alkenol, a lower alkynol or a phenol or amidated with an ammonia, a primary amine, or a secondary amine.

2. A benzoxazine derivative as claimed in claim 1 having the formula (IIa) or a salt thereof:

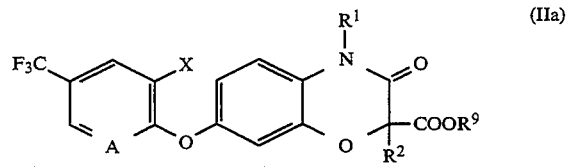

(IIa)

where A represents N or a CY group, where Y represents a hydrogen atom or a halogen atom;
X represents a chlorine atom;
$R^1$ represents a lower alkyl group which may also be substituted with a halogen atom;
$R^2$ represents a hydrogen atom or a lower alkyl group;
$R^9$ represents a hydrogen atom, a straight or branched lower alkyl group which may be also substituted, where the substituent may be either a halogen atom, a lower alkoxy group, a lower aliphatic acyl group, a lower alkoxycarbonyl group or a phenyl group, a lower alkenyl group, a lower alkynyl group or a phenyl group which may be also substituted, where the substituent may be either a halogen atom or a lower alkyl group.

3. A benzoxazine derivative as claimed in claim 1 having the formula (IIb) or a salt thereof:

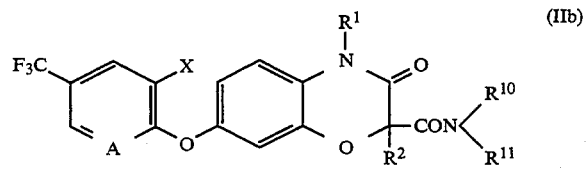

(IIb)

wherein A represents N or a CY group; where Y represents a hydrogen atom or a halogen atom;
X represents a chlorine atom;
$R^1$ represents a lower alkyl group which may be also substituted with a halogen atom;
$R^2$ represents a hydrogen atom or a lower alkyl group;
$R^{10}$ and $R^{11}$, which may be the same or different, each represent a hydrogen atom, a straight, branched or cyclic alkyl group having 1 to 10 carbon atoms which may be also substituted where the substituent may be either a halogen atom, a lower alkoxy group, a lower aliphatic acyl group, a lower alkoxycarbonyl group or a phenyl group, a lower alkenyl group, a lower alkynyl group, a phenyl group which may be also substituted, where the substituent may be either a halogen atom or a lower alkyl group or a pyrimidinyl group which may be also substituted, where the substituent may be either a halogen atom or a lower alkyl group.

4. A herbicide composition comprising a compound according to claim 1, as an active ingredient thereof and a carrier therefor.

* * * * *